United States Patent
Han et al.

(10) Patent No.: US 6,759,511 B2
(45) Date of Patent: Jul. 6, 2004

(54) COMPOUND USED AS AN AMINO-PROTECTING GROUP, PROCESS FOR PREPARING THE SAME, AND SYNTHETIC METHOD OF A PEPTIDE USING THE SAME

(75) Inventors: Hogyu Han, Seoul (KR); Nakcheol Jeong, Seoul (KR); SangJo Lee, Daejeon (KR); Jin Gab Oh, Daejon (KR); Hosung Yu, Daejeon (KR)

(73) Assignee: Hanchem Co., Ltd., Taejeon (KR)

( * ) Notice: Subject to any disclaimer, the term of this patent is extended or adjusted under 35 U.S.C. 154(b) by 44 days.

(21) Appl. No.: 10/284,387

(22) Filed: Oct. 31, 2002

(65) Prior Publication Data

US 2003/0220469 A1 Nov. 27, 2003

(30) Foreign Application Priority Data

May 16, 2002 (KR) .................................. 2002-0027133

(51) Int. Cl.⁷ ...................... C07C 69/96; C07C 69/767; C07D 233/40; C07K 1/06
(52) U.S. Cl. ................. 530/337; 548/334.1; 548/334.5; 558/272; 558/282; 558/283; 560/29; 560/32; 560/160; 560/163
(58) Field of Search ............................... 558/272, 282, 558/283; 560/29, 32, 160, 163; 548/334.1, 334.5; 530/337

(56) References Cited

U.S. PATENT DOCUMENTS 4,746,673 A * 5/1988 Imai et al. .................. 514/399

FOREIGN PATENT DOCUMENTS

WO 99/14269 A1 3/1999

OTHER PUBLICATIONS

"Recognition of DNA by Designed Ligands at Subnanomolar Concentrations", by John W. Trauger, Eldon E. Baird & Peter B. Dervan, NATURE, Aug. 8, 1996, vol. 382, pp. 559–561.

"The 9–Fluorenylmethoxycarbonyl Function, A New Base–Sensitive Amino–Protecting Group", By Louis A. Carpino and Grace Y. Han, Journal of the American Chemical Society, Sep. 23, 1970, 92:19, pp. 5748–5749.

"The 9–Fluorenylmethoxycarbonyl Amino–Protecting Group", by Louis A. Carpino and Grace Y. Han, Journal Org. Chem., 1972, vol. 37, No. 22, pp. 3404–3409.

* cited by examiner

Primary Examiner—Jeffrey Edwin Russel
(74) Attorney, Agent, or Firm—Birch, Stewart, Kolasch & Birch, LLP

(57) ABSTRACT

The present invention relates to a carbonic acid ester compound of the following formula (1):

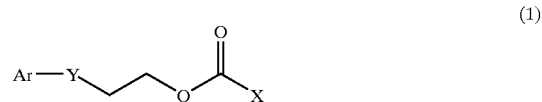

in which X, Y, and Ar are defined in the specification, which can be easily combined with the amino group of an amino acid or removed therefrom under mild conditions, whereby the amino group can be effectively protected during peptide syntheses, process for preparing the same, and use of the same. Since the amino acid derivatives thus protected have high thermal and chemical stabilities and good solubility for organic solvents, peptides can be synthesized at a low cost with a high yield.

11 Claims, No Drawings

COMPOUND USED AS AN AMINO-PROTECTING GROUP, PROCESS FOR PREPARING THE SAME, AND SYNTHETIC METHOD OF A PEPTIDE USING THE SAME

TECHNICAL FIELD

The present invention relates to a new compound which can be used as an amino-protecting group, a process for preparing the same, and a process for synthesizing peptides using the same. More specifically, the present invention relates to a carbonic acid ester compound of the following formula (1):

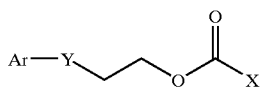

(1)

in which

X represents para-nitrophenyloxy, imidazolyl, Cl, or Br,

Y represents S or $SO_2$, and

Ar represents aryl group containing fluorine(s), which can be easily combined with the amino group of amino acids (capping or protection; 'capping' below) or removed therefrom (decapping or deprotection; 'decapping' below) under mild conditions, whereby the amino group can be effectively protected during peptide synthesis, a process for preparing the same, and a use of the same. Since the amino acid derivatives thus protected have high thermal and chemical stabilities and good solubility for organic solvents, peptides can be synthesized at a low cost with a high yield.

BACKGROUND ART

Typically known functional groups used for protecting the amino group of amino acids when preparing peptide compounds include tert-butoxycarbonyl (tBoc), 9-fluoroenylmethoxycarbonyl (Fmoc), 2-(4-nitrophenylsulfonyl)ethoxycarbonyl (Nsc), etc.

Among them, tBoc has a fatal demerit that it cannot be used for the amino acids having functional groups sensitive to acid because it should be removed by an acid.

Fmoc can be easily decapped from the amino group under weak basic conditions, which makes the peptide synthesis possible under much milder conditions than tBoc. However, Fmoc also has some fatal demerits. First, the amino acid derivatives protected by Fmoc have low thermal and chemical stabilities, which are particularly lowered in the case of amino acids containing aromatic groups. Therefore, in order to increase the yield of peptide synthesis from the aromatic amino acid derivatives protected by Fmoc group, short reaction time and excess amount of amino acid should be applied. Second, when it is used as a protecting group of amino acids containing a heterocycle, the low solubility of the amino acids in organic solvents may not be improved to a satisfactory level. Third, differently from tBoc, methyl or ethyl ester of amino acid cannot be used as a starting material, and t-butyl ester or carboxylic acid should be used as a starting material. Particularly, since decarboxylation may easily occur in the case of heterocycle compounds, carboxylic acid cannot be used, and t-butyl ester should be used. Since this t-butyl group should be removed under strong acidic conditions, however, it is practically impossible to use the protecting group of Fmoc for the heterocycle-containing amino acids. Fourth, the base piperidine used in the decapping step of Fmoc has weak reactivity with the resulting dibenzofulvene (DBF), and so has a limit in reducing side reactions by DBF by removing side products through a reaction.

On the other hand, since Nsc is more stable than Fmoc, it is useful for peptide synthesis. However, Nsc also has the disadvantage that it is inappropriate for the synthesis on a solid phase due to the low solubility in organic solvents depending on the kind of protected compounds.

DISCLOSURE OF THE INVENTION

Thus, the present inventors have extensively studied to provide a process for effectively synthesizing peptides, and so have identified that the new compound of formula (1) as defined above meets the inventor's requirements as an amino-protecting group. This new compound has the features that it has the advantage of Fmoc or Nsc, synthesis of peptides under weak basic conditions, and at the same time it cures the disadvantages thereof as illustrated above. That is, the amino acid derivatives protected by the amino-protecting group provided by the present invention have high thermal and chemical stabilities and good solubility for organic solvents; the cheap methyl or ethyl ester of amino acid can be used as a starting material in the peptide synthesis; and any side reaction by the products formed in the reaction for removing the protecting group does not occur.

Therefore, the object of the present invention is to provide the compound of formula (1) used as an amino-protecting group.

It is another object of the present invention to provide a process for preparing the compound of formula (1).

It is also another object of the present invention to provide a process for synthesizing peptides using the compound of formula (1) as a protecting group.

It is also another object of the present invention to provide an amino acid derivative protected by the compound of formula (1).

BEST MODE FOR CARRYING OUT THE INVENTION

First, the present invention relates to a new carbonic acid ester compound of the following formula (1):

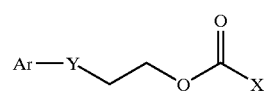

(1)

in which

X represents para-nitrophenyloxy, imidazolyl, Cl, or Br,

Y represents S or $SO_2$, and

Ar represents aryl group containing fluorine(s).

In the compound of formula (1), the substituent Ar defined as aryl group containing fluorine(s) preferably represents a radical selected from the following group:

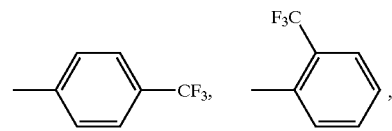

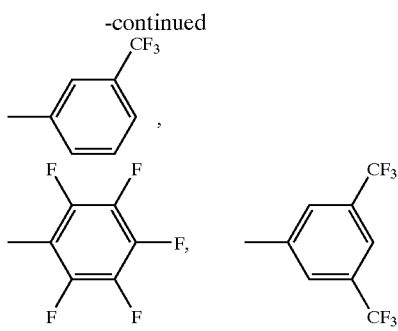

The carbonic acid ester compound of formula (1) according to the present invention, ① enables peptide synthesis under strong basic conditions, ② produces amino acid derivatives protected thereby, which have high thermal and chemical stabilities and good solubility for organic solvents, ③ enables use of the cheap methyl or ethyl ester of amino acid as a starting material in the peptide synthesis, ④ makes it easy to convert the peptides to unstable derivatives under basic conditions for easy decapping of the protecting group, and ⑤ does not cause any side reaction by the products formed in the decapping reaction.

The carbonic acid ester compound of formula (1) according to the present invention can be prepared by a process characterized in that a fluorinated derivative of aryl halide of the following formula (2):

in which Ar is defined as above and L represents a leaving group, preferably halogen, is reacted with mercaptoethanol to give a fluorinated derivative of 2-(arylsulfanyl)-ethanol of the following formula (3):

in which Ar is defined as above; and the resulting fluorinated derivative of 2-(arylsulfanyl)-ethanol of formula (3) is reacted with a compound of the following formula (4):

in which X is defined as above and L' represents a leaving group, preferably halogen, in order to introduce the para-nitrophenyloxy, imidazolyl, Cl, or Br group. Therefore, the present invention also relates to the above process for preparing the compound of formula (1).

Specifically, the fluorinated derivative of aryl chloride of formula (2) is dissolved in an organic solvent, mercaptoethanol is added thereto, and the mixture is reacted for 10~30 hours at 20~160° C. to give the fluorinated derivative 2-(arylsulfanyl)-ethanol of formula (3) (Step 1). Then, the compound of formula (3) thus obtained is dissolved in an organic solvent, the compound of formula (4) is added thereto, and the mixture is reacted for 1~5 hours at 0~100° C. to give the novel compound of formula (1) of the present invention (Step 2). For example, the reaction wherein 4-nitrophenyl chloroformate is used as the compound of formula (4) may be depicted as the following Reaction Scheme 1:

Reaction Scheme 1

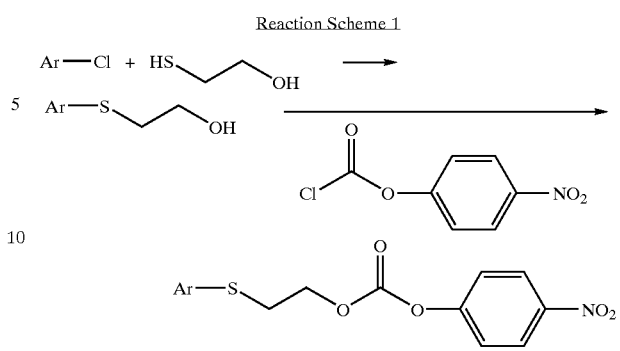

The present invention also provides a compound of the following formula (5),

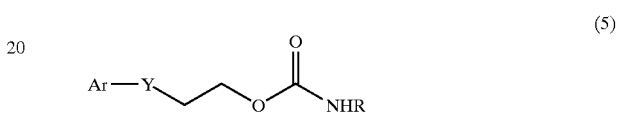

in which Ar and Y are defined as above, and R represents an amino acid except for the amino group combined with the α-carbon atom, which is an amino acid derivative of which amino group is protected by the carbonic acid ester compound of formula (1).

As stated in the following explanation on the capping step, the above compound of formula (5) is formed in the step of preparing a carbamate derivative of amino acid by reacting the compound of formula (1) according to the present invention with the amino group of an amino acid. When Y is S, the compound of formula (5) wherein Y is $SO_2$ may be obtained by additional oxidation reaction using a suitable oxidant.

The present invention also relates to a process for synthesizing peptides using the compound of formula (1) as an amino-protecting group. That is, the present invention relates to a process for synthesizing peptides comprising (A) the step of capping wherein the amino group of an amino acid is protected by the carbonic acid ester compound of formula (1) according to the present invention;

(B) the step of carboxylic acid formation wherein the amino acid derivative of which amino group is protected is hydrolyzed in case it is in the form of an ester;

(C) the step of peptide formation wherein carboxyl group of the amino acid derivative in the form of a carboxylic acid is coupled with amino group of another amino acid;

(D) the optional step of oxidation wherein S group at the position of Y in the capping moiety is oxidized to $SO_2$ group in case the position of Y in the capping moiety is S group; and (E) the step of decapping wherein the carbonic acid ester moiety is removed under basic conditions from the compound formed through the peptide formation step.

However, the oxidation step (D) may be positioned anywhere between the capping step (A) and the decapping step (E), and further the oxidation step (D) may be carried out simultaneously with the decapping step (E).

The peptide synthesizing process according to the present invention may be roughly divided into capping step, peptide formation step, and decapping step, which will be more specifically explained step by step below.

(1) Capping Step: Formation of Ttc Group

This step provides a carbamate derivative of an amino acid wherein the amino group is protected by the compound of formula (1).

In this capping step, the carbonic acid ester compound of formula (1) according to the present invention is reacted with an amino acid of formula (6) to give a carbamate derivative of an amino acid as represented by the above formula (5). This step may be more specifically depicted as Reaction Scheme 2 below:

Reaction Scheme 2

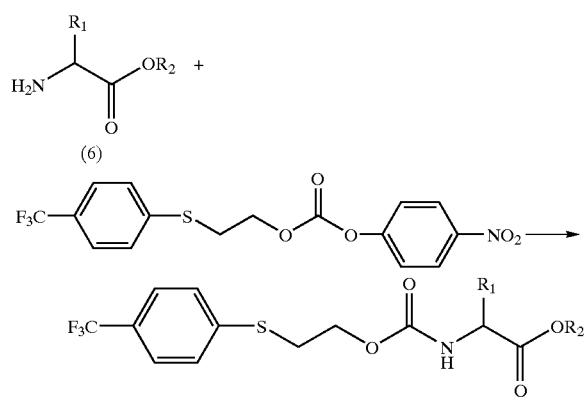

in which $R_1$ and $R_2$ each represent a substituent such as hydrogen, alkyl, aryl, or heterocycle which can be included in amino acids.

The capping group exemplified in the above Reaction Scheme 2 is 2-(4-trifluoromethylphenylthio)ethoxycarbonyl ('Ttc' below) which is stable against a base.

(2) Carboxylic Acid Formation Step

When the right side terminal of the above compound of formula (5), a carbamate derivative of capped amino acid, is not carboxylic acid, that is, when $R_2$ group is not hydrogen, the terminal is converted to carboxylic acid using a base. This step may be depicted, for example, as the following Reaction Scheme 3. In the following Reaction Scheme 3, the capping group is Ttc.

Reaction Scheme 3

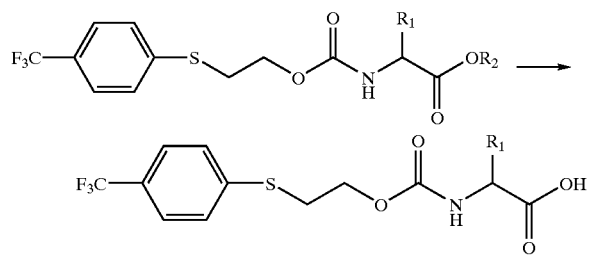

(3) Peptide Formation Step

Then, the carboxylic acid at the right terminal of the compound of formula (5) is reacted with an amino group of another amino acid to form a peptide bond and to give an amino acid dimer derivative such as the compound of the following formula (7).

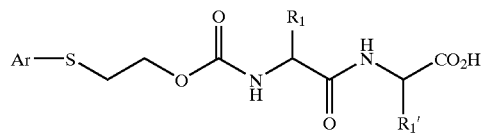

in which

Ar and $R_1$ are each defined as above, and $R_1'$ represents a substituent such as hydrogen, alkyl, aryl, or heterocycle which can be included in amino acids.

As the agent that can be used in the peptide bond formation of the above compound of formula (7), tetramethylfluoroformamidinium hexafluorophosphate(TFFH), bromo-tris-pyrrolidino-phosphonium-hexafluorophosphate (PyBroP), etc. may be mentioned, but not restricted thereto.

The above explained two steps (carboxylic acid formation step+peptide formation step) are repeated until the desired amino acid polymer (peptide) is obtained and finally the right terminal of the peptide derivative is converted to carboxylic acid.

(4) Oxidation Step: Formation of Tsc Group

At any time after the capping step, in case Y is S in the compound of formula (5), it can be oxidized to $SO_2$ in order to increase the sensitivity of the cap (carbonic acid ester compound) to the base. That is, as depicted in the following Reaction Scheme 4, the S moiety of the Ttc group is oxidized to $SO_2$ moiety.

Reaction Scheme 4

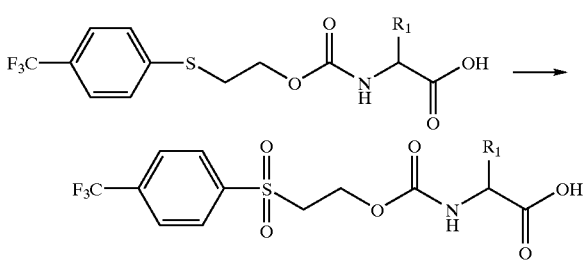

Specifically, the starting compound containing a thio group (—S—) is treated by hydrogen peroxide or a mixture of hydrogen peroxide and other oxidant in an organic solvent at a temperature ranging from $-10\sim100°$ C. to give an oxidized product containing a sulfonyl group (—$SO_2$—). The oxidized product as exemplified in the above Reaction Scheme 4 is a compound containing 2-(4-trifluoromethyl-benzenesulfonyl)ethoxycarbonyl ('Tsc' below) group, of which carbamate bond becomes very weak against a base.

The oxidation step can be performed at any time after the capping step, and if necessary, carried out simultaneously with the following decapping step.

(5) Decapping Step

To the compound obtained from the above explained oxidation step is added a secondary base such as piperidine, or a tertiary or aromatic base in an organic solvent in order to decompose the carbamate bond and to give a peptide of the following formula (8) in the decapping step:

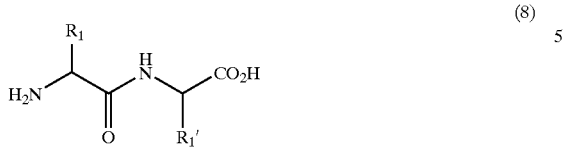
(8)

in which $R_1$ and $R_1'$ are each defined as above.

That is, in this step, the peptide compound synthesized through the peptide formation step is hydrolyzed under basic conditions as the case of Nsc, Fmoc, etc. to remove the carbonic acid ester moiety. For example, the Tsc group can be removed via β-hydrogen elimination reaction with 20% (v/v) piperidine in DMF solvent.

For reference, after the protecting group Tsc is decapped by piperidine, the resulting products are analyzed by NMR. As a result, as depicted in the following Reaction Scheme 5, only the compound of formula (10) is detected as the decapping product, and the compound of formula (9), a side product of the β-hydrogen elimination reaction, is not.

Reaction Scheme 5

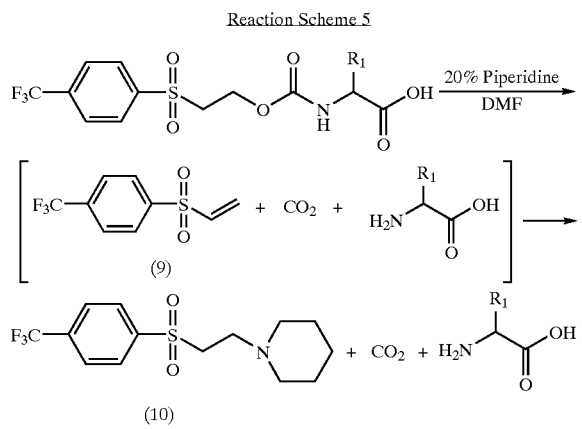

Therefore, since such compounds that may cause side reactions in the decapping step as the compound of formula (9) are not produced in the process according to the present invention, the desired peptide can be more effectively obtained than in the previous process using the Fmoc group.

The present invention will be more specifically explained in the following examples. However, it should be understood that the following examples are intended to illustrate the present invention but not to limit the scope of the present invention in any manner. Further, a person skilled in the art may easily modify the reactants and reaction conditions in the following examples within a reasonable range, and such modifications also fall within the technical scope of the present invention.

Usually, there is a problem of solubility decrease of the reactants (intermediates) to the solvent in the artificial synthesis of peptides. Therefore, in order to confirm that there is no problem caused by the solubility decrease of the reactants (intermediates) in the process of the present invention, amino acids having such N-containing heterocycles as pyrrole or imidazole, that is, those having low solubility, are particularly selected and used as the reactants in the following examples.

The full names of the abbreviations used in the following examples are as follows:

EA: ethyl acetate
DMF: dimethylformamide
DCM: dichloromethane
DIEA: diisopropylethylamine
HOBt: 1-hydroxybenzotriazole
THF: tetrahydrofuran
TFFH: tetramethylfluoroformamidinium hexafluorophosphate
DMAP: 4-(N,N-dimethylamino)pyridine
PyBroP: bromo-tris-pyrrolidino-phosphonium-hexafluorophosphate

EXAMPLE 1

Preparation of the Carbonic Acid Ester Compound According to the Present Invention The carbonic acid ester compound according to the present invention was prepared by a 2-step reaction.

(1) Step 1: Preparation of 2-(4-trifluoromethyl-phenylsulfanyl)-ethanol

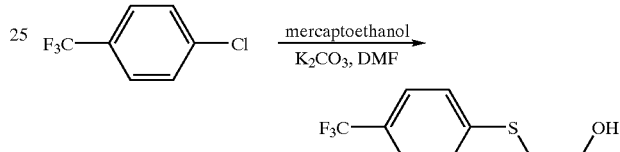

4-Chlorobenzotrifluoride (31.36 ml, 235.26 mmol) was dissolved in anhydrous DMF (200 ml), and mercaptoethanol (15.00 ml, 213.87 mmol) and $K_2CO_3$ (38.43 g, 278.06 mmol) were added thereto. The mixture was stirred for 30 minutes at room temperature and then refluxed. After 15 hours have passed, the reaction mixture was cooled to room temperature and the reaction was stopped by adding distilled water. The reaction mixture was extracted with diethyl ether, and the organic layer was washed with aqueous $NH_4Cl$ solution, dried over anhydrous $MgSO_4$, and concentrated. The reaction solution thus concentrated was purified by silica gel column chromatography (EA/n-hexane=1/3, v/v) to give 2-(4-trifluoromethyl-phenylsulfanyl)-ethanol (32.11 g, 67.56%) of a colorless oil.

TLC (EA/n-hexane=1/1, v/v) $R_f$=0.45

$^1H$ NMR (CDCl$_3$) δ 7.53 (d, J=8.4 Hz, 2H), 7.42 (d, J=8.4 Hz, 2H), 3.82 (t, 2H), 3.20 (t, 2H), 2.15 (brs, 1H)

$^{13}C$ NMR (CDCl$_3$) 140.60, 129.38, 128.48, 128.04, 127.62, 127.18, 125.74, 125.69, 125.64, 125.59, 122.18, 118.58, 60.36, 35.84

(2) Step 2: Preparation of carbonic acid 4-nitro-phenyl ester 2-(4-trifluoromethyl-phenylsulfanyl)-ethyl ester

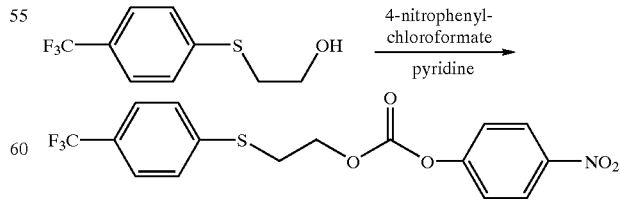

2-(4-Trifluoromethyl-phenylsulfanyl)ethanol (15.00 g, 67.50 mmol) prepared in the above Step (1) was dissolved in anhydrous DCM (100 ml), pyridine (7.59 ml, 93.81 mmol) and 4-nitrophenyl chloroformate (13.61 g, 67.50 mmol) were added thereto at 0° C. in order, and the mixture was stirred for 2 hours at room temperature. The reaction was stopped by adding distilled water, and the reaction mixture was extracted with DCM. The organic layer thus extracted was washed with aqueous NH$_4$Cl solution, dried over anhydrous MgSO$_4$, and then concentrated. The concentrate was purified by silica gel column chromatography (DCM/n-hexane=5/1, v/v) to give carbonic acid 4-nitrophenyl ester 2-(4-trifluoromethyl-phenylsulfanyl)-ethyl ester (22.54 g, 86.21%) of a pale yellow oil.

TLC (EA/n-hexane=1/3, v/v) R$_f$:0.37

$^1$H NMR (CDCl$_3$) δ 8.27 (d, J=9.3 Hz, 2H), 7.56 (d, J=8.7 Hz, 2H), 7.47 (d, J=8.1 Hz, 2H), 7.36 (d, J=8.7 Hz, 2H), 4.47 (t, 2H), 3.35 (t, 2H)

$^{13}$C NMR (CDCl$_3$) 155.05, 152.08, 145.24, 139.89, 129.29, 128.75, 128.32, 128.17, 127.89, 127.45, 125.87, 125.82, 125.77, 125.72, 125.69, 125.15, 122.09, 121.55, 118.48, 66.78, 30.95

EXAMPLE 2

Peptide Preparation I According to the Process of the Present Invention

Peptides were prepared using a pyrrole-type amino acid as follows.

(1) Capping Step

<Preparation of 1-methyl-4-[2-(4-trifluoromethyl-phenylsulfanyl)ethoxycarbonylamino]-1H-pyrrole-2-carboxylic acid methyl ester>

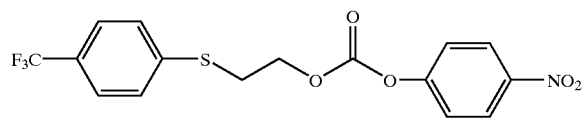

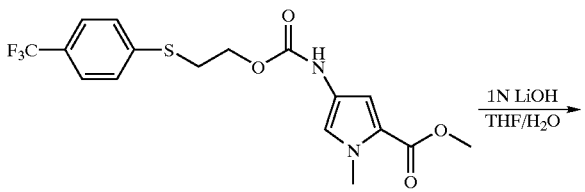

After 1-methyl-4-nitropyrrole-2-carboxylic acid methyl ester (1.17 g, 6.35 mmol) was dissolved in EA (20 ml), 10% Pd/C (50 mg, catalytic weight) was added thereto. The mixture was stirred for 1 hour at room temperature under hydrogen atmosphere to reduce a nitro group (NO$_2$) into an amino group (NH$_2$), whereby a pyrrole-type amino acid was obtained. 10% Pd/C was filtered out by celite 545 filter, and the filtrate was washed with EA and MeOH and concentrated under vacuum. To the residue were added carbonic acid 4-nitro-phenyl ester 2-(4-trifluoromethyl-phenylsulfanyl)-ethyl ester (2.23 g, 5.76 mmol) dissolved in anhydrous DCM (30 ml), DIEA (2.01 μm, 11.56 mmol), DMAP (1.41 g, 11.56 mmol), and HOBt (1.77 g, 11.56 mmol), and the mixture was stirred for 12 hours at room temperature. The reaction was stopped by adding water and the reaction mixture was extracted with DCM. The organic layer was dried over anhydrous MgSO$_4$ and concentrated. The residue was purified by silica gel column chromatography (EA/n-hexane=1/3, v/v) to give methyl 1-methyl-4-[2-(4-trifluoromethyl-phenylsulfanyl)-ethoxycarbonylamino]-1H-pyrrole-2-carboxylate (1.98 g, 85.42%) of a pale yellow solid.

TLC (EA/n-hexane=1/3; v/v) R$_f$:0.13

$^1$H NMR (CDCl$_3$) δ 7.54 (d, J=8.4 Hz, 2H), 7.54 (d, J=8.1 Hz, 2H), 7.05 (s, 1H), 6.65 (s, 1H), 6.39 (brs, 1H), 4.33 (t, 2H), 3.88(s, 3H), 3.80 (s, 3H), 3.26 (t, 2H)

$^{13}$C NMR (CDCl$_3$) 161.35, 153.24, 140.79, 129.37, 128.40, 127.97, 127.65, 127.53, 127.10, 125.77, 125.73, 125.67, 125.62, 122.16, 121.33, 119.97, 118.56, 108.26, 63.00, 51.01, 36.61, 31.22

(2) Peptide Formation Step 1: Formation of Carboxyl Group

<Preparation of 1-methyl-4-[2-(4-trifluoromethyl-phenylsulfanyl)ethoxycarbonylamino]-1H-pyrrole-2-carboxylic acid>

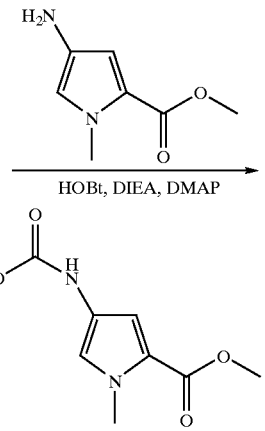

-continued

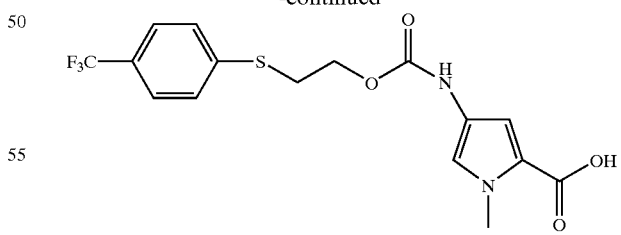

Methyl 1-methyl-4-[2-(4-trifluoromethyl-phenylsulfanyl)-ethoxycarbonylamino]-1H-pyrrole-2-carboxylate (5.0 g, 12.43 mmol) prepared in the capping step was dissolved in THF/H$_2$O (200 ml/100 ml), 1N LiOH (30 ml) was added thereto, and the mixture was stirred for 4 days at room temperature. The reaction solution was acidified to pH 2.0 by 1N HCl and then extracted with EA and water. The organic layer was washed with aqueous NaCl solution and dried over anhydrous MgSO$_4$. The solvent contained therein was removed to give a white solid, which was then recrystallized from EA and n-hexane to give 1-methyl-4-[2-(4-trifluoromethyl-phenylsulfanyl)-ethoxy carbonylamino]-1H-pyrrole-2-carboxylic acid (3.20 g, 66.29%) of a pale yellow solid.

TLC (EA/n-hexane=1/1, v/v) R$_f$:0.23

$^1$H NMR (DMSO-d$_6$) δ 12.17 (brs, 1H), 9.46 (brs, 1H), 7.65 (d, J=8.4 Hz, 2H), 7.56 (d, J=8.4 Hz, 2H), 7.03 (s, 1H), 6.62 (d, J=1.5 Hz, 1H), 4.24 (t, J=6.5 Hz, 2H), 3.78 (s, 3H), 3.37 (t, J=6.6 Hz, 2H)

$^{13}$C NMR (DMSO-d$_6$) 161.92, 153.18, 141.95, 129.71, 127.09, 126.43, 126.11, 126.00, 125.79, 125.75, 125.57, 125.15, 122.51, 121.35, 120.01, 118.91, 107.72, 61.97, 36.13, 30.35

(3) Oxidation Step: Formation of Tsc Group

<Preparation of 1-methyl-4-[2-(4-trifluoromethyl-benzenesulfonyl)ethoxycarbonylamino]-1H-pyrrole-2-carboxylic acid>

1-Methyl-4-[2-(4-trifluoromethyl-phenylsulfanyl)-ethoxycarbonylamino]-1H-pyrrole-2-carboxylic acid (3.00 g, 7.7 mmol) prepared in Step (2) was dissolved in acetone (90 ml), Na$_2$MoO$_4$ (2.40 ml of 0.3 M solution) and H$_2$O$_2$ (4.50 ml of 30% solution) were added thereto in order, and the mixture was stirred at room temperature. After 72 hours have passed, the resulting white precipitate was filtered and washed with acetone and EA to give 1-methyl-4-[2-(4-trifluoromethyl-benzenesulfonyl)ethoxycarbonylamino]-1H-pyrrole-2-carboxylic acid (2.10 g, 64.81%) of a white solid.

TLC (EA/n-hexane=4/1, v/v) R$_f$=0.38

$^1$H NMR (DMSO-d$_6$) δ 12.15 (brs, 1H), 9.21 (brs, 1H), 8.14 (d, J=8.1 Hz, 2H), 8.00 (d, J=8.1 Hz, 2H), 6.95 (s, 1H), 6.56 (s, 1H), 4.34 (t, J=5.6 Hz, 2H), 3.84 (t, j=5.4 Hz, 2H), 3.77 (s, 3H)

$^{13}$C NMR (DMSO-d$_6$) 161.82, 152.46, 143.27, 134.09, 133.66, 133.23, 132.80, 128.78, 126.64, 126.60, 125.16, 122.00, 121.54, 119.86, 118.84, 117.94, 107.67, 57.47, 54.23, 36.08

HRMS (FAB) for C$_{16}$H$_{15}$F$_3$N$_2$O$_6$S (M$^+$), calcd 420.0603, found 420.0609

(4-1) Peptide Formation Step 2: Example 1 of Peptide Bond Formation

<Preparation of 1-methyl-4-({1-methyl-4-[2-(4-trifluoromethyl-benzenesulfonyl)-ethoxycarbonylamino]-1H-pyrrole-2-carbonyl}-amino)-1H-pyrrole-2-carboxylic acid methyl ester>

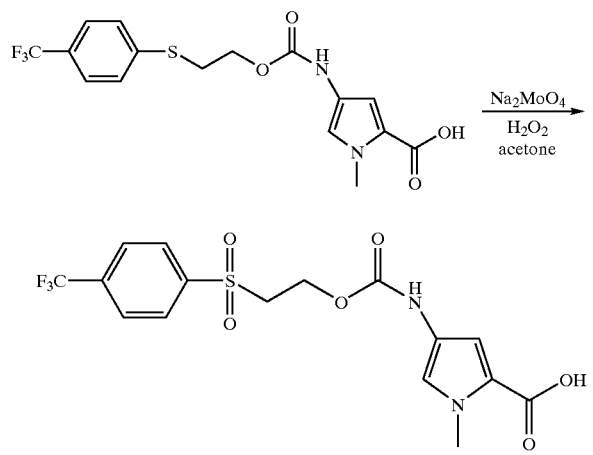

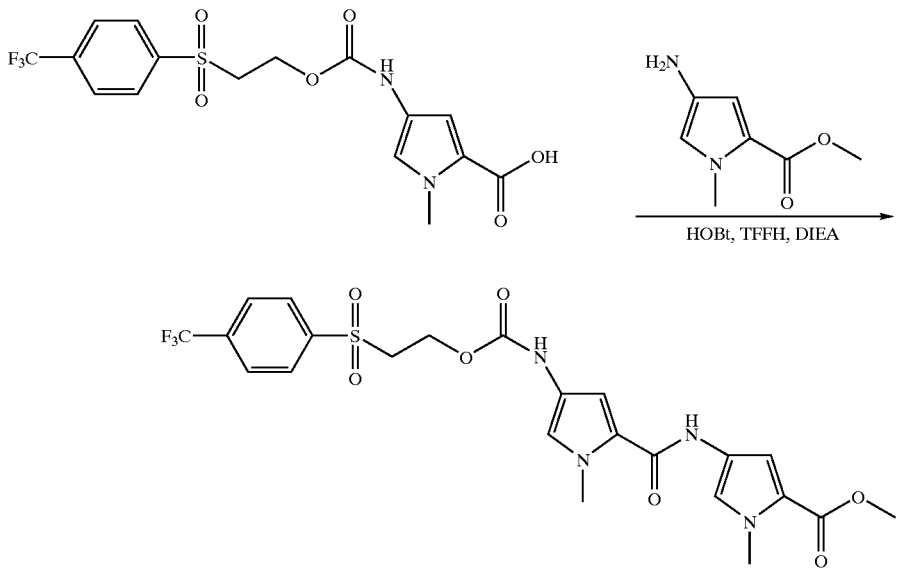

To a solution of 1-methyl-4-nitropyrrole-2-carboxylic acid methyl ester (65.68 mg, 0.3567 mmol) in EA (10 ml) was added 10% Pd/C (10 mg). The reaction solution was stirred for 10 hours at room temperature under hydrogen atmosphere to reduce a nitro group ($NO_2$) into an amino group ($NH_2$), whereby a pyrrole-type amino acid was obtained. 10% Pd/C was filtered out by celite 545 and the filtrate was washed with EA and methanol. 1-Methyl-4-[2-(4-trifluoromethyl-benzenesulfonyl)-ethoxycarbonylamino]-1H-pyrrole-2-carboxylic acid (49.98 mg, 0.1189 mmol) dissolved in a solvent mixture of anhydrous DMF (6 ml) and DCM (2 ml) was added thereto, TFFH (94.21 mg, 0.3567 mmol), HOBt (64.73 mg, 0.4756 mmol) and DIEA (82.84 ml, 0.4748 mmol) were also added thereto, and the reaction solution was stirred for 8 hours at room temperature. Distilled water was added to the reaction solution, which was then extracted with diethyl ether. The organic layer was dried over anhydrous $MgSO_4$ and concentrated. The concentrate was purified by silica gel column chromatography (EA/n-hexane=3/1, v/v) to give 1-methyl-4-({1-methyl-4-[2-(4-trifluoromethyl-benzene-sulfonyl)-ethoxycaronlylamino]-1H-pyrrole-2-carbonyl}-amino)-1H-pyrrole-2-carboxylic acid methyl ester (41.70 mg, 62.99%) of a pale yellow solid.

TLC (EA/n-hexane=3/1, v/v) $R_f$=0.43

$^1$H NMR (DMSO-$d_6$+CDCl$_3$) δ 9.87 (s, 1H), 8.34 (s, 1H), 8.15 (d, J=8.1 Hz, 2H), 8.03 (d, J=8.1 Hz, 2H), 7.45 (d, J=1.8 Hz, 1H), 6.89 (d, J=1.5 Hz, 1H), 6.84 (s, 1H), 6.79 (s, 1H), 4.36 (bt, 2H), 3.84 (m, 8H), 3.73 (s, 3H)

(4-2) Peptide Formation Step 2: Example 2 of Peptide Bond Formation

<Preparation of 1-methyl-4-({1-methyl-4-[2-(4-trifluoromethyl-benzenesulfonyl)ethoxycarbonylamino]-1H-pyrrole-2-carbonyl}-amino)-1H-imidazole-2-carboxylic acid ethyl ester>

1-Methyl-4-nitroimidazole-2-carboxylic acid ethyl ester (71.05 mg, 0.3567 mmol) was dissolved in EA (10 ml) and 10% Pd/C (10 mg, catalytic weight) was added thereto. The reaction solution was stirred for 10 hours at room temperature under hydrogen atmosphere to reduce a nitro group ($NO_2$) into an amino group ($NH_2$), whereby an imidazole-type amino acid was obtained. 10% Pd/C was filtered out by celite 545 and the filtrate was washed with EA and methanol. 1-Methyl-4-[2-(4-trifluoromethyl-benzenesulfonyl)-ethoxycarbonylamino]-1H-pyrrole-2-carboxylic acid (49.98 mg, 0.1189 mmol) dissolved in a solvent mixture of anhydrous DMF (6 ml) and DCM (2 ml) was added thereto, PyBroP (166.29 mg, 0.3567 mmol) and DIEA (62.13 ml, 0.3567 mmol) were also added thereto, and the reaction solution was reacted according to the same procedure as Step (4-1) of Example 2 to give 1-methyl-4-({1-methyl-4-[2-(4-trifluoromethyl-benzenesulfonyl)ethoxycarbonylamino]-1H-pyrrole-2-carbonyl}-amino)--1H-imidazole-2-carboxylic acid ethyl ester (51.05 mg, 75.12%) of a pale yellow solid.

TLC (EA/n-hexane=3/1, v/v) $R_f$=0.23

$^1$H NMR (CDCl$_3$) δ 8.33 (s, 1H), 8.10 (d, J=8.1 Hz, 2H), 7.86 (d, J=8.1 Hz, 2H), 7.54 (s, 1H), 6.90 (s, 1H), 6.45 (s, 1H), 4.51 (t, J=7.2 Hz, 2H), 4.40 (q, J=7.2 Hz, 2H), 4.00 (s, 3H), 3.91 (s, 3H), 3.56 (t, J=5.7 Hz, 2H), 1.41 (t, J=7.2 Hz, 3H)

EXAMPLE 3

Peptide Preparation II According to the Process of the Present Invention

Peptides were prepared using an imidazole-type amino acid which is different from the amino acid of Example 2 as follows.

(1) Capping Step

<Preparation of 1-methyl-4-[2-(4-trifluoromethylphenylsulfanyl)ethoxycarbonylamino]-1H-imidazole-2-carboxylic acid ethyl ester>

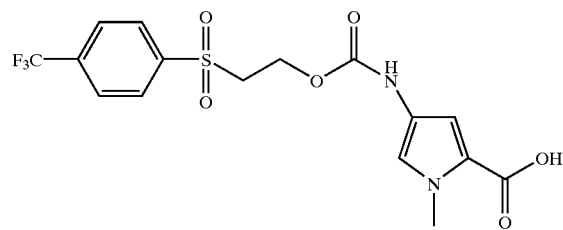 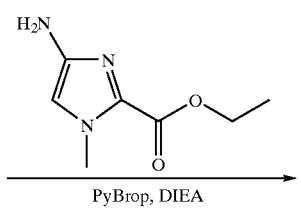

PyBrop, DIEA

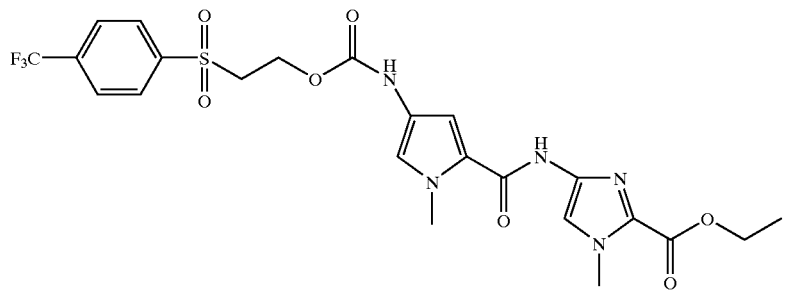

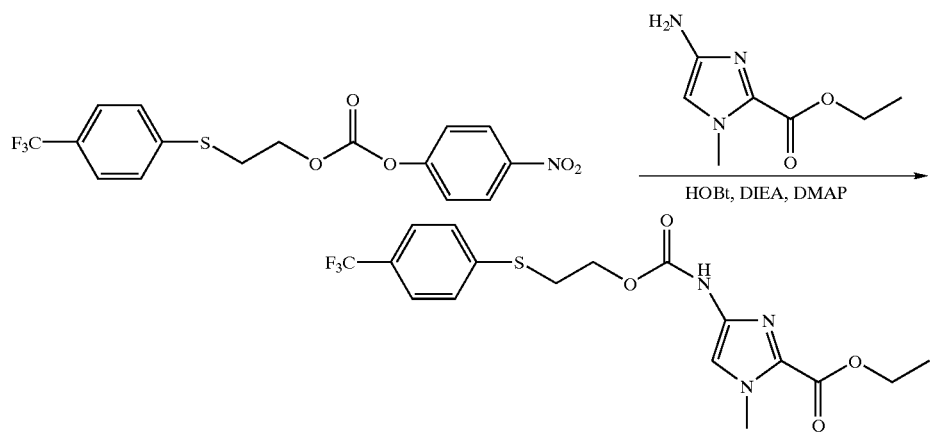

After 1-methyl-4-nitroimidazole-2-carboxylic acid ethyl ester (2.56 g, 12.85 mmol) was dissolved in EA (20 ml), 10% Pd/C (100 mg, catalytic weight) was added thereto. The mixture was stirred for 10 hours at room temperature under hydrogen atmosphere to reduce a nitro group ($NO_2$) into an amino group ($NH_2$), whereby an imidazole-type amino acid was obtained. 10% Pd/C was filtered out by celite 545 filter, and the filtrate was washed with EA and MeOH, and concentrated. To the residue were added carbonic acid 4-nitro-phenyl ester 2-(4-trifluoromethyl-phenylsulfanyl)-ethyl ester (4.52 g, 11.67 mmol) dissolved in anhydrous DCM (40 ml), DIEA (4.06 ml, 23.32 mmol), DMAP (2.85 g, 23.32 mmol), and HOBt (3.57 g, 23.32 mmol), and the mixture was stirred at room temperature. After 12 hours have passed, the reaction was stopped by adding water and the reaction mixture was extracted with DCM. The organic layer was dried over anhydrous $MgSO_4$ and concentrated. The residue was purified by silica gel column chromatography (EA/n-hexane=1/2, v/v) to give 1-methyl-4-[2-(4-trifluoromethyl-phenylsulfanyl)-ethoxycarbonylamino]-1H-imidazole-2-carboxylic acid ethyl ester (3.77 g, 77.40%) of a white solid.

TLC (EA/n-hexane=1/2) $R_f$:0.14

$^1$H NMR ($CDCl_3$) δ 7.54 (d, J=8.4 Hz, 2H), 7.45 (d, J=8.1 Hz, 2H), 7.31 (brs, 1H), 7.23 (s, 1H), 4.40 (q, J=6.9 Hz, 3H), 4.33 (t, J=7.2 Hz, 2H), 4.00 (s, 3H), 3.26 (t, J=6.9 Hz, 2H), 1.41 (t, J=7.1 Hz, 2H)

$^{13}$C NMR ($CDCl_3$) 158.50, 152.57, 140.52, 136.92, 131.58, 129.27, 128.33, 127.89, 127.67, 127.46, 127.03, 125.79, 125.75, 125.70, 125.65, 122.07, 118.47, 113.15, 63.33, 61.48, 36.05, 31.10, 14.39

(2) Peptide Formation Step 1: Formation of Carboxyl Group

<Preparation of 1-methyl-4-[2-(4-trifluoromethyl-phenylsulfanyl)ethoxycarbonylamino]-1H-imidazole-2-carboxylic acid>

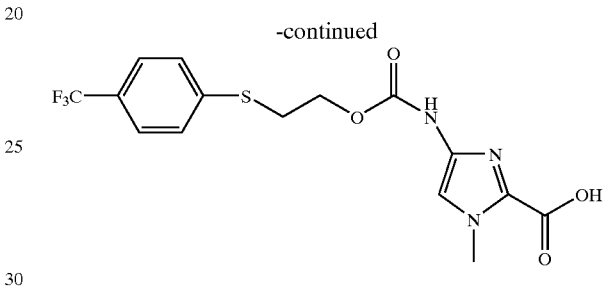

Ethyl 1-methyl-4-[2-(4-trifluoromethyl-phenylsulfanyl)-ethoxycarbonylamino]-1H-imidazole-2-carboxylate (0.69 g, 1.65 mmol) prepared in the capping step was dissolved in $THF/H_2O$ (27.40 ml/13.70 ml), 1N LiOH (4.57 ml) was added thereto, and the mixture was stirred at room temperature. After 15 hours have passed, the reaction solution was acidified to pH 2.0 by 1N HCl and then extracted with EA and water. The organic layer was washed with aqueous NaCl solution, dried over anhydrous $MgSO_4$, and concentrated. The residue was recrystallized from EA and n-hexane to give 1-methyl-4-[2-(4-trifluoromethyl-phenylsulfanyl)-ethoxycarbonylamino]-1H-imidazole-2-carboxylic acid (0.52 g, 80.94%) of a white solid.

TLC (EA/MeOH/$H_2O$=24/5/4, v/v/v) $R_f$:0.33

$^1$H NMR (DMSO-$d_6$) δ.10.15 (brs, 1H), 7.65 (d, J=8.4 Hz, 2H), 7.57 (d, J=8.1 Hz, 2H), 7.28 (s, 1H), 4.25 (t, J=6.6 Hz, 2H), 3.88 (s, 3H), 3.36 (t, J=6.5 Hz, 2H)

$^{13}$C NMR (DMSO-$d_6$) 160.02, 153.24, 141.94, 137.34, 132.06, 129.70, 127.14, 126.39, 126.10, 125.96, 125.78, 125.73, 125.54, 125.11, 122.50, 118.90, 113.61, 62.33, 35.51, 30.19

(3) Oxidation Step: Formation of Tsc Group

<Preparation of 1-methyl-4-[2-(4-trifluoromethyl-benzenesulfonyl)ethoxycarbonylamino]-1H-imidazole-2-carboxylic acid>

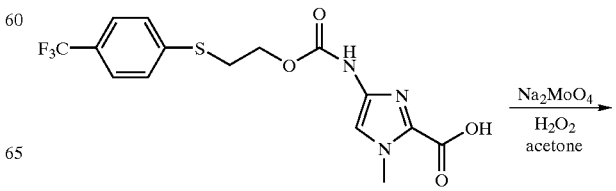

-continued

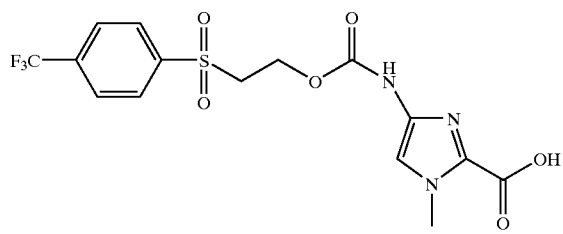

1-Methyl-4-[2-(4-trifluoromethyl-phenylsulfanyl)-ethoxycarbonylamino]-1H-imidazole-2-carboxylic acid (1.00 g, 2.57 mmol) prepared in Step (2) was dissolved in acetone (30 ml), $Na_2MoO_4$ (0.80 ml of 0.3 M solution) and $H_2O_2$ (1.50 ml of 30% solution) were added thereto, and the mixture was stirred at room temperature. After 72 hours have passed, the resulting precipitate was filtered and washed with acetone and EA to give 1-methyl-4-[2-(4-trifluoromethyl-benzenesulfonyl)-ethoxycarbonylamino]-1H-imidazole -2-carboxylic acid (0.73 g, 67.59%) of a white solid.

TLC ($EA/MeOH/H_2O=24/5/4$, v/v/v) $R_f=0.17$ $^1$H NMR (DMSO-$d_6$) δ 9.82 (brs, 1H), 8.14 (d, J=7.8 Hz, 2H), 8.00 (d, J=7.8 Hz, 2H), 7.94 (brs, 1H), 7.06 (s, 1H), 4.36 (brs, 2H), 3.87 (brs, 3H)

$^{13}$C NMR (DMSO-$d_6$) 160.04, 152.50, 143.22, 136.96, 134.04, 133.61, 133.18, 132.75, 132.32, 128.86, 126.60, 125.14, 121.52, 117.93, 113.22, 56.97, 54.15, 35.43

HRMS (FAB) for $C_{15}H_{14}F_3N_3O_6S$ (M+Na$^+$), calcd 444.0375, found 444.0464

(4-1) Peptide Formation Step 2: Example 1 of Peptide Bond Formation

<Preparation of 1-methyl-4-({1-methyl-4-[2-(4-trifluoromethyl-benzenesulfonyl)ethoxycarbonylamino]-1H-imidazole-2-carbonyl}-amino)-1H-pyrrole-2-carboxylic acid methyl ester>

1-Methyl-4-nitropyrrole-2-carboxylic acid methyl ester (65.68 mg, 0.3567 mmol) was dissolved in EA (10 ml) and 10% Pd/C (10 mg) was added thereto. The reaction solution was stirred for 10 hours at room temperature under hydrogen atmosphere to reduce a nitro group ($NO_2$) into an amino group ($NH_2$), whereby a pyrrole-type amino acid was obtained. 10% Pd/C was filtered out by celite 545 and the filtrate was washed with EA and methanol. 1-Methyl-4-[2-(4-trifluoromethyl-benzenesulfonyl)-ethoxycarbonylamino]-1H-imidazole-2-carboxylic acid (50.10 mg, 0.1187 mmol) dissolved in a solvent mixture of anhydrous) MF (6 ml) and DCM (2 ml) was added thereto, TFFH (83.37 mg, 0.3567 mmol), HOBt (64.73 mg, 0.4748 mmol) and DIEA (82.84 ml, 0.4748 mmol) were also added thereto, and the reaction solution was reacted according to the same procedure as Step (4-1) of Example 2 to give 1-methyl-4-({1-methyl-4-[2-(4-trifluoromethyl-benzenesulfonyl)ethoxycarbonylamino]-1H-imidazole-2-carbonyl}-amino)-1H-pyrrole-2-carboxylic acid methyl ester (41.7 mg, 63.01%) of a pale yellow solid.

TLC (EA/n-hexane=3/1, v/v) $R_f=0.48$ $^1$H NMR (CDCl$_3$) δ 8.86 (s, 1H), 8.09 (d, J=8.1 Hz, 2H), 7.85 (d, J=8.1 Hz, 2H), 7.42 (d, J=2.4 Hz, 1H), 7.15 (s, 1H), 7.05 (s, 1H), 6.81 (d, J=1.8 Hz, 1H), 4.52 (bt, 2H), 4.04 (s, 3H), 3.91 (s, 3H), 3.81 (s, 3H), 3.56 (bt, 2H)

(4-2) Peptide Formation Step 2: Example 2 of Peptide Bond Formation

<Preparation of 1-methyl-4-({1-methyl-4-[2-(4-trifluoromethyl-benzenesulfonyl)-ethoxycarbonylamino]-1H-imidazole-2-carbonyl}-amino)-1H-imidazole-2-carboxylic acid ethyl ester>

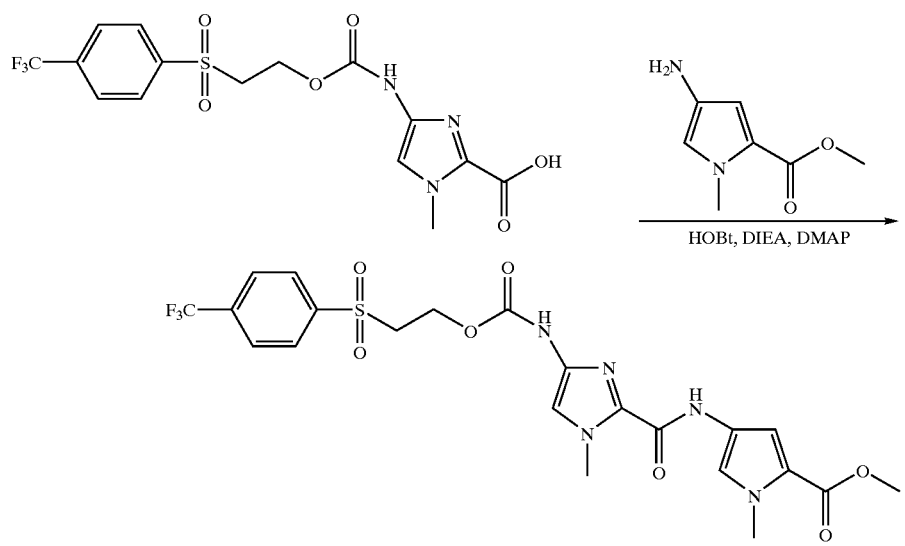

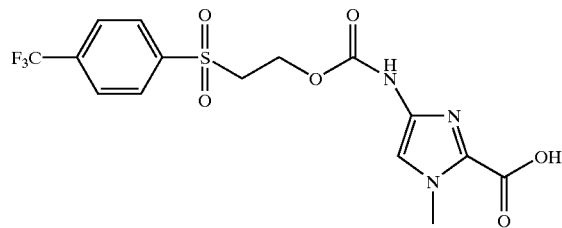
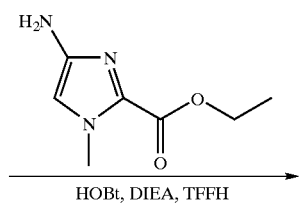

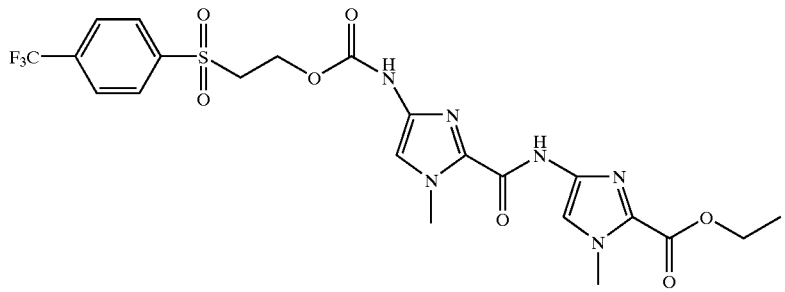

1-Methyl-4-nitroimidazole-2-carboxylic acid ethyl ester (71.05 mg, 0.3567 mmol) was dissolved in EA (10 ml) and 10% Pd/C (10 mg, catalytic weight) was added thereto. The reaction solution was stirred for 10 hours at room temperature under hydrogen atmosphere to reduce a nitro group ($NO_2$) into an amino group ($NH_2$), whereby an imidazole-type amino acid was obtained. 10% Pd/C was filtered out by celite 545 and the filtrate was washed with EA and methanol. 1-Methyl-4-[2-(4-trifluoromethyl-benzenesulfonyl)-ethoxycarbonylamino]-1H-imidazole-2-carboxylic acid (50.10 mg, 0.1187 mmol) dissolved in a solvent mixture of anhydrous DMF (6 ml) and DCM (2 ml) was added thereto, TFFH (94.21 mg, 0.3567 mmol), HOBt (64.74 mg, 0.4748 mmol) and DIEA (82.85 ml, 0.4748 mmol) were also added thereto, and the reaction solution was reacted according to the same procedure as Step (4-1) of Example 2 to give 1-methyl-4-({1-methyl-4-[2-(4-trifluoromethyl-benzenesulfonyl)-ethoxycarbonylamino]-1H-imidazole-2-carbonyl}-amino)-1H-imidazole-2-carboxylic acid ethyl ester (37.00 mg, 54.45%) of a pale yellow solid.

TLC (EA/n-hexane=3/1, v/v) $R_f$=0.26

$^1$H NMR ($CDCl_3$) δ 9.42 (s, 1H), 8.09 (d, J=8.1 Hz, 2H), 7.85 (d, J 8.1 Hz, 2H), 7.55 (s, 1H), 7.09 (s, 1H), 7.07 (s, 1H), 4.52 (bt, 2H), 4.42 (q, J=7.2 Hz, 2H, 4.03 (s, 3H), 4.02 (s, 3H), 3.57 (t, J=6.0 Hz, 2H), 1.44 (t, J=7.1 Hz, 3H)

EXAMPLE 4

Confirmation of a Side Reaction During the Decapping Step in the Process According to the Present Invention It was indirectly confirmed whether any side reaction occurs during the decapping step in the process of synthesizing peptides according to the present invention. That is, it was confirmed in the decapping step using a base, for example, piperidine, which one is produced between the compound of formula (9) that is a side product of β-hydrogen elimination reaction, and the compound of formula (10) of a piperidine derivative (see Reaction Scheme 5) as follows.

To 1-methyl-4-[2-(4-trifluoromethyl-benzenesulfonyl)-ethoxycarbonylamino]-1H-imidazole-2-carboxylic acid (30 mg, 0.07 mmol) was added 20% piperidine (DMF/2 ml) and the mixture was stirred for 0.5 hour at room temperature. The reaction solution was extracted with water and diethyl ether, and then the organic layer was dried over anhydrous $MgSO_4$ and concentrated. The residue was purified by silica gel column chromatography (EA/n-hexane=1/1, v/v) to give a white solid (22.6 mg, 99%).

The compound thus obtained was analyzed by NMR. As a result, a side product was identified to be 1-[2-(4-trifluoromethyl-benzenesulfonyl)-ethyl]-piperidine. That is, it can be seen that a piperidine derivative is produced as a side product in the decapping step as depicted in the following reaction scheme:

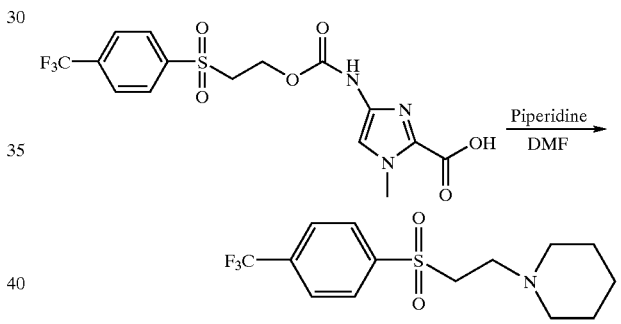

The characteristics of the side product thus obtained are as follows.

TLC (EA/n-hexane=1/1, v/v) $R_f$=0.38

$^1$H NMR ($CDCl_3$) δ 8.07 (d, J=8.4 Hz, 2H), 7.83 (d, J=8.4 Hz, 2H), 3.34 (t, 2H), 2.74 (t, 2H), 2.27 (s, 4H), 1.35 (s, 6H)

$^{13}$C NMR ($CDCl_3$) 128.65, 126.12, 126.07, 126.02, 125.97, 54.08, 53.62, 51.95, 25.66, 23.97

Therefore, since such a side product causing a side reaction as the compound of formula (9) is not produced in the process according to the present invention, the desired peptides can be more effectively prepared in the present invention than in the earlier process using Fmoc group.

Industrial Applicability

Peptides can be effectively synthesized if the carbonic acid ester compound of formula (1) according to the present invention is used as a protecting group.

Since the protecting groups Ttc and Tsc provided by the present invention may be easily decapped in the presence of a base, the earlier peptide synthesizing process using Fmoc may also be applied to the present invention as it is.

The amino acid derivative capped by the protecting group according to the present invention has high thermal and chemical stabilities and good solubility for organic solvents. Therefore, the protecting group of the present invention can be used for aromatic or heterocycle-containing amino acids as well as aliphatic amino acids.

Further, the peptide synthesis according to the present invention is economic since the cheap methyl or ethyl ester of amino acid can be used as a starting material.

What is claimed is:

1. A carbonic acid ester compound of the following formula (1):

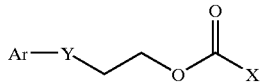
(1)

in which

X represents para-nitrophenyloxy, imidazolyl, Cl, or Br,

Y represents S or $SO_2$, and

Ar represents aryl group containing fluorine(s).

2. The compound of claim 1 wherein Ar is any one radical selected from the following group:

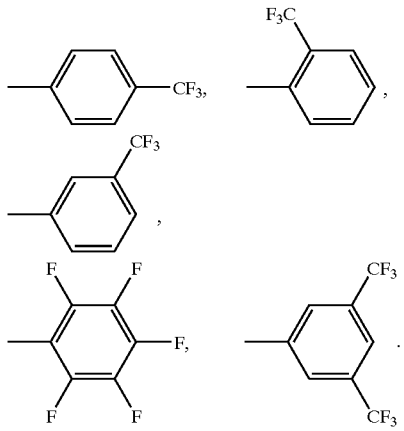

3. A process for preparing the carbonic acid ester compound of formula (1) as defined in claim 1 characterized in that a fluorinated derivative of aryl halide of the following formula (2):

Ar—L     (2)

in which Ar is defined as claim 1 and L represents a leaving group, is reacted with mercaptoethanol to give a fluorinated derivative of 2-(arylsulfanyl)-ethanol of the following formula (3):

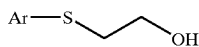
(3)

in which Ar is defined as claim 1; and the resulting fluorinated derivative of 2-(arylsulfanyl)-ethanol of formula (3) is reacted with a compound of the following formula (4):

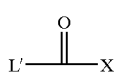
(4)

in which X is defined as claim 1 and L' represents a leaving group.

4. The process of claim 3 wherein L and L' are each halogen.

5. The process of claim 4 wherein L is chlorine.

6. A process for protecting the amino group of an amino acid using the carbonic acid ester compound of formula (1) as defined in claim 1.

7. An amino acid derivative of the following formula (5):

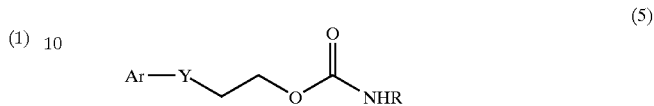
(5)

in which Ar and Y are defined as claim 1 and R represents an amino acid except for the amino group combined with the α-carbon atom, wherein the amino group is protected by the carbonic acid ester compound of formula (1) as defined in claim 1.

8. The compound of claim 7 wherein Ar is any one radical selected from the following group:

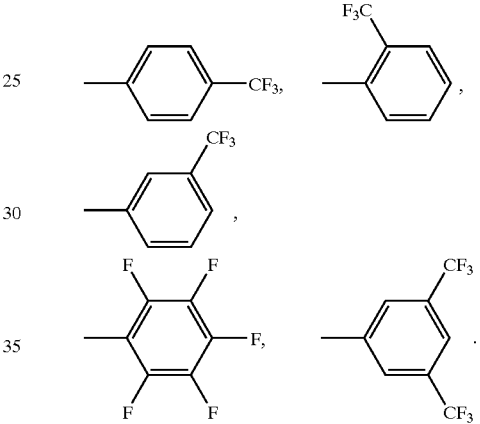

9. A process for synthesizing peptides comprising (A) the step of capping wherein the amino group of an amino acid is protected by the carbonic acid ester compound of formula (1) according to claim 1;

(B) the step of carboxylic acid formation wherein the amino acid derivative of which amino group is protected is hydrolyzed in case it is in the form of an ester;

(C) the step of peptide formation wherein carboxyl group of the amino acid derivative in the form of a carboxylic acid is coupled with amino group of another amino acid;

(D) the optional step of oxidation wherein S group at the position of Y in the capping moiety is oxidized to $SO_2$ group in case the position of Y in the capping moiety is S group; and (E) the step of decapping wherein the carbonic acid ester moiety is removed under basic conditions from the compound formed through the peptide formation step.

10. The process of claim 9 wherein the oxidation step (D) is positioned anywhere between the capping step (A) and the decapping step (E).

11. The process of claim 9 wherein the oxidation step (D) is carried out simultaneously with the decapping step (E).

* * * * *